United States Patent
Carson et al.

(10) Patent No.: US 8,101,761 B2
(45) Date of Patent: *Jan. 24, 2012

(54) (E)-N-{3-[1-(8-FLUORO-11H-10-OXA-1-AZA-DIBENZO [A,D] CYCLOHEPTEN-5YLIDENE)-PROPYL]-PHENYL}-METHANESULFONA-MIDE AS GLUCOCORTICOID RECEPTOR MODULATOR FOR THE TREATMENT OF RHEUMATOID ARTHRITIS

(75) Inventors: Matthew William Carson, Fishers, IN (US); Michael Joseph Coghlan, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/810,886

(22) PCT Filed: Jan. 8, 2009

(86) PCT No.: PCT/US2009/030374

§ 371 (c)(1),
(2), (4) Date: Jun. 28, 2010

(87) PCT Pub. No.: WO2009/089312

PCT Pub. Date: Jul. 16, 2009

(65) Prior Publication Data

US 2010/0280062 A1    Nov. 4, 2010

Related U.S. Application Data

(60) Provisional application No. 61/020,520, filed on Jan. 11, 2008.

(51) Int. Cl.
C07D 455/03 (2006.01)
C07D 313/10 (2006.01)
A61K 31/4353 (2006.01)

(52) U.S. Cl. ............... 546/80; 546/89; 546/93; 514/291

(58) Field of Classification Search .................... 546/80, 546/89, 93; 514/291
See application file for complete search history.

(56) References Cited

U.S. PATENT DOCUMENTS

| | | | |
|---|---|---|---|
| 4,999,363 A | 3/1991 | Oshima et al. | |
| 5,024,912 A | 6/1991 | Neishi et al. | |
| 5,093,210 A | 3/1992 | Ohta et al. | |
| 5,378,701 A | 1/1995 | Ohshima et al. | |
| 2010/0069425 A1 | 3/2010 | Carson et al. | |

FOREIGN PATENT DOCUMENTS

| | | |
|---|---|---|
| JP | 01161245 | 6/1989 |
| WO | 9933786 | 7/1999 |
| WO | 0059884 | 10/2000 |
| WO | 2004043965 | 5/2004 |
| WO | 2004052847 | 6/2004 |
| WO | 2008008882 | 1/2008 |

OTHER PUBLICATIONS

Carson, "New Vistas in the Search for a Selective Glucocorticoid Receptor Modulator (SGRM)," Oral Presentation at Cambridge Health Institute, Cambridge, MA, Oct. 18, 2007.
Coghlan, "Nuclear Hormone Receptor Research," Oral Presentation at 28th Gulf Coast Chemistry Conference, Pensacola, FL, Aug. 24, 2006.
Jadhav, "Discovery of orally bioavailable, nonsteroidal mineralocorticoid receptor antagonists: A tale of three platforms," Oral Presentation at ACS National Meeting, Atlanta, GA, Mar. 25-30, 2006.
Jadhav, "Discovery of First, Orally Bioavailable, Nonsteroidal Mineralocorticoid Receptor Antagonist," Oral Presentation at Gordon Research Conference, Newport, RI, Jul. 4-9, 2004.
Yu, et al., "Cyclocarbopalldation of Alkynes: A Stereoselective Method for Preparing Dibenzoxapine Containing Tetrasubstituted Exocyclic Alkenes," Organic Letters, vol. 8, No. 8, pp. 1685-1688 (2006).
Yu, "Stereoselective Synthesis of Dibenzoxapine Containing Nuclear Hormone Receptor Modulators through Palladium-Catalyzed Cascade Reactions," Oral Presentation at Gordon Research Conference, Smithfield, RI, Jul. 16-21, 2006.
International Preliminary Report on Patentability for PCT/US2007/073345, dated Jan. 22, 2009.
European Patent Office Examination Report for pending Application No. 07799520.7 (PCT/US2007/073345), dated May 15, 2009.
Applicant Response to EPO Examination Report for pending Application 07799520.7 (PCT/US2007/073345), dated Sep. 23, 2009.
European Patent Office Examination Report for Application No. 07799520.7 (PCT/US2007/073345), dated Mar. 17, 2010.
Examination Report Summary for Pakistan Application No. 1419/2007 (PCT/US2007/073345), dated Mar. 5, 2010.

*Primary Examiner* — Rita Desai
(74) *Attorney, Agent, or Firm* — Elizabeth Dingess-Hammond; Alexander Wilson

(57) ABSTRACT

The present invention provides Compound (I) or a pharmaceutically acceptable salt thereof; pharmaceutical compositions comprising Compound (I) in combination with one or more pharmaceutically acceptable carriers, excipients, or diluents; and discloses methods for the treatment of inflammatory and immune disorders comprising administering to a patient in need thereof an effective amount of Compound (I) or a pharmaceutically acceptable salt thereof.

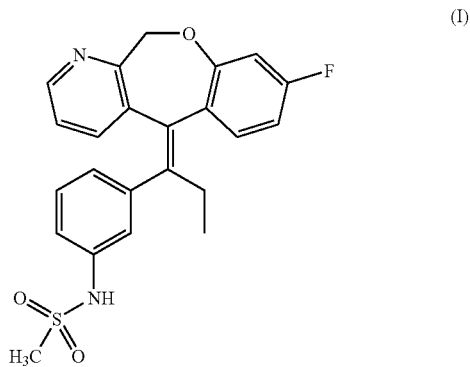

(I)

6 Claims, No Drawings

(E)-N-{3-[1-(8-FLUORO-11H-10-OXA-1-AZA-DIBENZO [A,D] CYCLOHEPTEN-5YLIDENE)-PROPYL]-PHENYL}-METHANESULFONAMIDE AS GLUCOCORTICOID RECEPTOR MODULATOR FOR THE TREATMENT OF RHEUMATOID ARTHRITIS

This application is a 371 of PCT/US2009/030374, filed Jan. 8, 2009, which claims the benefit of 61/020,520, filed Jan. 11, 2008.

The present invention relates to therapeutic agents for the treatment or prevention of inflammatory and immune disorders responsive to steroidal glucocorticoids, to pharmaceutical compositions comprising the agents, to methods of treating or preventing inflammatory and immune disorders in patients, and to intermediates and processes useful in the synthesis of the therapeutic agents.

Naturally occurring as well as synthetic steroidal glucocorticoids have been widely used for over fifty years for the treatment of acute and chronic inflammatory and immune disorders such as rheumatoid arthritis, osteoarthritis, rheumatic fever, asthma, allergic rhinitis, systemic lupus erythematosus, chronic obstructive pulmonary disease, Crohn's disease, inflammatory bowel disease, and ulcerative colitis. However, the use of glucocorticoids is often associated with severe and sometimes irreversible side effects such as bone loss/osteoporosis, hyperglycemia, diabetes mellitus, hypertension, glaucoma, muscle atrophy, Cushing's syndrome, and psychosis. Thus, there remains a need for alternative therapies which possess the beneficial effects of steroidal glucocorticoids, but with a reduced likelihood or incidence of attendant side effects.

Glucocorticoids regulate gene transcription after the formation of a complex with the glucocorticoid receptor (GR). Following glucocorticoid binding, the GR-glucocorticoid complex translocates to the cell nucleus where it binds to glucocorticoid hormone response elements (GREs) in the promoter regions of particular genes. The GR-glucocorticoid/GRE complex then, in turn, activates (transactivation) or inhibits transcription of proximally located genes. Alternatively, the GR-glucocorticoid complex may negatively regulate gene transcription by a process that does not involve DNA binding. In this process, termed transrepression, the GR-glucocorticoid complex enters the nucleus and directly interacts (via protein-protein interaction) with other transcription factors, repressing their ability to induce gene transcription and thus protein expression.

The search for GR ligands suitable as replacements for steroidal glucocorticoids is hindered by the fact that the other steroid hormone receptors, for example the androgen receptor (AR), the mineralocorticoid receptor (MR), and the progesterone receptor (PR), which mediate other physiological processes, have ligand binding domains homologous to GR. As a result, GR ligands have a potential for cross reactivity with these other receptors. Thus, a desired attribute of a replacement for steroidal glucocorticoids is that it binds to GR with greater affinity relative to the other steroid hormone receptors.

Recent insights demonstrate that the anti-inflammatory effects of glucocorticoids can be maintained in the absence of GR binding to DNA. As a consequence, mechanisms of glucocorticoid action mediated predominantly by GR protein-protein interactions (e.g. transrepression) are believed to be sufficient to induce the anti-inflammatory response. Furthermore, many side effects of glucocorticoid therapy (e.g. hyperglycemia, diabetes mellitus, glaucoma, and muscle atrophy) are now believed to be predominantly mediated by transactivational mechanisms following GR binding to DNA. Thus, an agent which is capable of differentiating GR-mediated transrepression from GR-mediated transactivation is particularly desirable. Furthermore, an agent that displays limited capacity to modulate (i.e. agonize, partially agonize, partially antagonize, or antagonize) the transcriptional activity of the other steroid hormone receptors is also particularly desirable.

It is an object of the present invention to provide an agent which binds to GR with greater affinity relative to the other steroid hormone receptors. More particularly it is an object to provide an agent which binds to GR with more than 10-fold greater affinity relative to AR, MR, and PR. It is a further object of the present invention to provide an agent which possesses potent anti-inflammatory properties relative to its propensity for inducing side effects associated with glucocorticoid therapy. More particularly, it is an object to provide an agent which possesses potent anti-inflammatory properties relative to its propensity for inducing bone loss or osteoporosis. It is a further object of the present invention to provide an agent which displays limited capacity to modulate the activity of other steroid hormone receptors, AR, MR, and PR.

GR modulators are known in the art. For example WO 04/052847 discloses a genus of tricyclic steroid hormone receptor modulators which are useful for treating disorders susceptible to mineralocorticoid receptor or glucocorticoid receptor modulation. Surprisingly, it has now been found that by selecting a compound from within the scope of WO 04/052847, which is provided as Compound (I) herein below, a novel therapeutic agent has been identified which possesses an unexpected profile of activity that suggests it is particularly useful in the treatment of inflammatory and immune disorders responsive to steroidal glucocorticoids.

Accordingly, the present invention provides Compound (I):

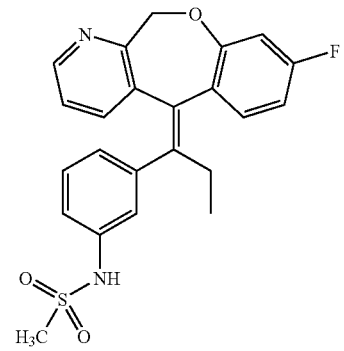

Compound (I)

(E)-N-{3-[1-(8-Fluoro-11H-10-oxa-1-aza-dibenzo[a,d]cyclohepten-5-ylidene)-propyl]-phenyl}-methanesulfonamide or a pharmaceutically acceptable salt thereof.

In another embodiment, the present invention provides a method of treating or preventing an inflammatory or immune disorder, particularly rheumatoid arthritis, comprising administering to a patient in need thereof an effective amount of Compound (I), or a pharmaceutically acceptable salt thereof. In addition, the present invention provides Compound (I), or a pharmaceutically acceptable salt thereof, for use in therapy. The present invention also provides Compound (I), or a pharmaceutically acceptable salt thereof, for use in the treatment or prevention of an inflammatory or immune disorder, particularly rheumatoid arthritis.

In another embodiment, the present invention provides the use of Compound (I), or a pharmaceutically acceptable salt thereof, for the manufacture of a medicament for treating an inflammatory or immune disorder, particularly rheumatoid arthritis.

In another embodiment, the present invention provides a pharmaceutical composition comprising Compound (I), or a pharmaceutically acceptable salt thereof, in combination with one or more pharmaceutically acceptable carriers, excipients, or diluents. As a preferred embodiment, the present invention provides a pharmaceutical composition for the treatment or prevention of rheumatoid arthritis comprising Compound (I), or a pharmaceutically acceptable salt thereof, in combination one or more pharmaceutically acceptable carriers, excipients, or diluents. In addition, the present invention also provides novel intermediates and processes for the synthesis of Compound (I).

The present invention provides the use of Compound (I) for the treatment or prevention of inflammatory and immune disorders responsive to steroidal glucocorticoids. Such disorders include, for example, rheumatoid arthritis, osteoarthritis, rheumatic fever, asthma, allergic rhinitis, systemic lupus erythematosus, chronic obstructive pulmonary disease, Crohn's disease, inflammatory bowel disease, and ulcerative colitis. A particular disorder for which Compound (I) is useful is rheumatoid arthritis. Rheumatoid arthritis (RA) is a chronic disorder characterized by persistent joint synovial tissue inflammation with a typical age of onset between 30 and 50 years of age. RA is the most common form of inflammatory arthritis with women being twice as likely as men to develop the disease.

The use of Compound (I) for the treatment or prevention of inflammatory and immune disorders is also believed to be associated with a reduced propensity, likelihood, or incidence of side effects typically associated with glucocorticoid therapy. One such side effect of glucocorticoid therapy is bone loss/osteoporosis or glucocorticoid induced osteoporosis (GIOP). GIOP is the most common cause of drug induced osteoporosis and has been reported to occur in up to fifty percent of patients undergoing chronic (i.e. lasting longer than six months) glucocorticoid therapy. In particular, the use of Compound (I) is believed to be associated with a reduced propensity, likelihood, or incidence of bone loss or osteoporosis.

Unless otherwise defined, this invention includes pharmaceutically acceptable salts of Compound (I), as well as solvates of the free base of Compound (I) and the pharmaceutically acceptable salts thereof. However, the free base of Compound (I) is preferred. The term "pharmaceutically acceptable salt" as used herein, refers to salts of Compound (I) which are substantially non-toxic to living organisms. Examples of pharmaceutically acceptable salts and methods for their preparation are conventional in the art. See for example, Stahl et al., "Handbook of Pharmaceutical Salts Properties, Selection and Use", VCHA/Wiley-VCH, (2002); Gould, P. L., "Salt selection for basic drugs", *International Journal of Pharmaceutics,* 33: 201-217 (1986); and Bastin et al. "Salt Selection and Optimization Procedures for Pharmaceutical New Chemical Entities", *Organic Process Research and Development,* 4: 427-435 (2000).

As used herein the term "patient" refers to a human or nonhuman mammal such as a dog, cat, cow, monkey, horse, or sheep. More particularly, the term "patient" refers to a human. The term "treating" (or "treat" or "treatment") as used herein includes prohibiting, preventing, restraining, slowing, stopping, or reversing the progression or severity of an existing symptom or disorder. The term "preventing" (or "prevent" or "prevention") as used herein refers to prohibiting, restraining, or inhibiting the incidence or occurrence of a symptom or disorder.

Compound (I), or a pharmaceutically acceptable salt thereof, may be formulated for administration as part of a pharmaceutical composition. As such, pharmaceutical compositions comprising Compound (I), or a pharmaceutically acceptable salt thereof, in combination with one or more pharmaceutically acceptable carriers, excipients, or diluents are an important embodiment of the invention. Examples of pharmaceutical compositions and methods for their preparation are well known in the art. See, e.g. REMINGTON: THE SCIENCE AND PRACTICE OF PHARMACY, A. Gennaro, et al., eds., 19$^{th}$ ed., Mack Publishing (1995). Illustrative compositions comprising Compound (I) include, for example: Compound (I) in suspension with 1% sodium carboxymethyl cellulose, 0.25% polysorbate 80, and 0.05% Antifoam 1510™ (Dow Corning); and Compound (I) in suspension with 0.5% methylcellulose, 1% sodium lauryl sulfate, and 0.1% Antifoam 1510 in 0.01N HCl. A preferred composition of the present invention comprises Compound (I), or a pharmaceutically acceptable salt thereof formulated in a capsule or tablet.

Compound (I), or compositions comprising Compound (I) can be administered by any route which makes Compound (I) bioavailable, including oral and parenteral routes. For example, Compound (I), or compositions comprising Compound (I) can be administered orally, subcutaneously, intramuscularly, intravenously, transdermally, intranasally, rectally, buccally, and the like. Alternatively, the compound may be administered by continuous infusion. It is understood, however, that oral administration is a preferred route of administration.

As used herein the term "effective amount" refers to the amount or dose of Compound (I) which, upon single or multiple dose administration to the patient, provides the desired effect in the patient under diagnosis or treatment. An effective amount can be readily determined by the attending diagnostician, as one skilled in the art, by considering a number of factors such as the species of mammal; its size, age, and general health; the specific disease involved; the degree or severity of the disease; the response of the individual patient; the particular compound administered; the mode of administration; the bioavailability characteristics of the preparation administered; the dose regimen selected; and the use of any concomitant medications.

Biological Activity

As used herein, "Kd" refers to the equilibrium dissociation constant for a ligand-receptor complex; "Ki" refers to the equilibrium dissociation constant for drug-receptor complex, and is an indication of concentration of drug that will bind to half the binding sites at equilibrium; "IC$_{50}$" refers to the concentration of an agent which produces 50% of the maximal inhibitory response possible for that agent or, alternatively, to the concentration of an agent which produces 50% displacement of ligand binding to the receptor; "EC$_{50}$" refers to the concentration of an agent which produces 50% of the maximal response possible for that agent; and "ED$_{50}$" refers to the dose of an administered therapeutic agent which produces 50% the maximal response for that agent.

Nuclear Hormone Receptor Binding Assays:

Cell lysates from human embryonic kidney HEK293 cells overexpressing human GR (glucocorticoid receptor), AR (androgen receptor), MR (mineralocorticoid receptor), or PR (progesterone receptor) are used for receptor-ligand competition binding assays to determine Ki values.

Briefly, steroid receptor competition binding assays are run in a buffer containing 20 mM Hepes buffer (pH=7.6), 0.2 mM EDTA, 75 mM NaCl, 1.5 mM MgCl$_2$, 20% glycerol, 20 mM sodium molybdate, 0.2 mM DTT (dithiothreitol), 20 μg/ml aprotinin and 20 μg/ml leupeptin. Typically, steroid receptor binding assays include radio-labeled ligands, such as 0.3 nM [$^3$H]-dexamethasone for GR binding, 0.36 nM [$^3$H]-methyltrienolone for AR binding, 0.25 nM [$^3$H]-aldosterone for MR binding, and 0.29 nM [$^3$H]-methyltrienolone for PR binding, and either 20 μg 293-GR lysate, 22 μg 293-AR lysate, 20 μg 293-MR lysate or 40 μg 293-PR lysate per well. Assays are typically run in 96-well format. Competing test compounds are added at various concentrations ranging from about 0.01 nM to 10 μM. Non-specific binding is determined in the presence of 500 nM dexamethasone for GR binding, 500 nM aldosterone for MR binding, or 500 nM methyltrienolone for AR and PR binding. The binding reactions (140 μL) are incubated overnight at 4° C., then 70 μl of cold charcoal-dextran buffer (containing per 50 ml of assay buffer, 0.75 g of charcoal and 0.25 g of dextran) is added to each reaction. Plates are mixed for 8 minutes on an orbital shaker at 4° C. The plates are then centrifuged at 3,000 rpm at 4° C. for 10 minutes. An aliquot of 120 μl of the binding reaction mixture is then transferred to another 96-well plate and 175 μl of Wallac Optiphase Hisafe 3™ scintillation fluid is added to each well. Plates are sealed and shaken vigorously on an orbital shaker. After an incubation of 2 hours, plates are read in a Wallac Microbeta counter.

The data are used to calculate an estimated $IC_{50}$ and percentage inhibition at 10 μM. The Kd for [$^3$H]-dexamethasone for GR binding, [$^3$H]-methyltrienolone for AR binding, [$^3$H]-aldosterone for MR binding, or [$^3$H]-methyltrienolone for PR binding, are determined by saturation binding. The $IC_{50}$ values for compounds are converted to Ki using the Cheng-Prusoff equation.

Binding assay protocols similar to those described above can be readily designed by the ordinarily skilled artisan. Following procedures essentially as described above, Compound (I) displayed a Ki in the GR binding assay of about 0.2 nM; a Ki in the AR binding assay of about 6.7 nM; a Ki in the MR binding assay of about 9.2 nM; and a Ki in the PR binding assay of about 32 nM (values reported as means of n=7 experiments). Thus, Compound (I) is a potent ligand of human GR and, furthermore, binds to GR with about 15-fold or more greater affinity relative to each of human MR, AR, and PR.

To demonstrate the ability of compounds of the present invention to modulate the activity of steroid hormone receptors (i.e. either agonize, partially agonize, partially antagonize, or antagonize), bioassays are performed which detect functional modulation of target gene expression in cells transiently transfected with a nuclear receptor protein and a hormone response element-reporter gene construct. The solvents, reagents, and ligands employed in the functional assay are readily available from commercial sources, or can be prepared by one of ordinary skill in the art.

Nuclear Hormone Receptor Functional Modulation Assays:

Human embryonic kidney HEK293 cells are transfected with steroid hormone receptor and reporter gene plasmids using Fugene™ transfection reagent. Briefly, the reporter plasmid containing two copies of probasin ARE and TK(thymidine kinase) promoter upstream of the luciferase reporter cDNA, is transfected into HEK293 cells with a plasmid constitutively expressing human androgen receptor (AR) using viral CMV(cytomegalovirus) promoter. The reporter plasmid containing two copies of GRE and TK promoter upstream of the luciferase reporter cDNA is transfected with a plasmid constitutively expressing either human glucocorticoid receptor (GR), human mineralocorticoid receptor (MR), or human progesterone receptor (PR) using viral CMV promoter. Cells are transfected in T150 cm flasks in Dulbecco's modified eagle medium (DMEM) with 5% charcoal-stripped fetal bovine serum (FBS). After an overnight incubation, transfected cells are trypsinized, plated in 96 well dishes in DMEM media containing 5% charcoal-stripped FBS, incubated for 4 hours and then exposed to various concentrations of test compounds ranging from about 0.01 nM to 10 μM. In the antagonist mode for the assays, low concentrations of agonist for each respective receptor are added to the media (0.25 nM dexamethasone for GR, 0.3 nM of methyltrienolone for AR, 0.05 nM of promegestone for PR and 0.05 nM aldosterone for MR). After 24-hours incubation with test compounds, cells are lysed and luciferase activity is determined using standard techniques.

Data are fitted to a four parameter-fit logistic curve fit to determine $EC_{50}$ values. The percentage efficacy (compounds with saturated maximum responses) or the percent maximum stimulation (compounds with maximum responses that do not saturate) are determined relative to maximum stimulation obtained with the following reference agonists: 100 nM methyltrienolone for AR assay, with 30 nM promegestone for PR assay, with 30 nM aldosterone for MR assay and with 100 nM dexamethasone for GR assay. $IC_{50}$ values may be determined similarly using antagonist mode assay data. Percent inhibitions may also be determined relative to the response in the presence of agonist alone, as described above.

Following procedures essentially as described above, Compound (I) displayed the following profile in activating transcription: for GR, about 44% efficacy with an $EC_{50}$ of about 1.8 nM; for AR, about 4.4% efficacy with an $EC_{50}$ greater than 10 μM; for MR, about 11% efficacy with an $EC_{50}$ greater than 10 μM; and for PR, about 54% efficacy with an $EC_{50}$ greater than 10 μM (values reported as means of n=4 or 5 experiments).

Glucocorticoid Receptor-mediated Transrepression Assays
1. IL-1,3-stimulated IL-6 Production in Human Skin Fibroblast CCD-39SK Cells:

Briefly, human skin fibroblast CCD-39SK cells (20,000 cells/well), obtained from ATCC are seeded in 96-well plates in serum-free growth medium supplemented with 10% FBS, 100 U/ml penicillin, 100 ug/ml streptomycin and 2 mmol/L L-glutamine. Cells are maintained in a humidified chamber with 5% $CO_2$ at 37° C. Test compounds are added to the wells in various concentrations ranging from a final concentration of about 4.65 μM to 4.64 μM. 0.1 μM of dexamethasone is used as a positive control. 1-hour post treatment with test compound, IL-1β is added at final concentration of 1 ng/ml; and the reaction mixture is incubated overnight. 10 μl of supernatant is removed from each well and IL-6 concentrations are determined using an ELISA kit, with IL-6 concentrations being quantified by reading absorbance at 450 nm.

2. LPS-Stimulated TNF-α Production in PMA-Differentiated U937 Cells:

Human U937 pre-monocytic cells, obtained from ATCC, are grown in complete RPMI 1640 medium containing 10% FBS. To allow monocytes to differentiate to adherent macrophages, U937 cells are washed in calcium, magnesium free and resuspended in fresh RPMI medium containing 20 nM phorbol 12-myristate-13-acetate (PMA) overnight. After differentiation, test compounds are added to the cells in the 96-well plate at various concentrations ranging from about 4.65 pM to 4.64 μM. 1-hour post treatment with test compound, LPS is added at final concentration of 100 ng/ml and the reaction mixture is incubated overnight. 25 μl cell-free supernatant is transferred from each well to another 96-well plate and TNF-α production is measured using an ELISA kit with TNF-α being quantified by reading absorbance at 450 nm.

Following procedures essentially as described above, Compound (I) induces about 90% or greater maximal inhibition of the endogenous expression of IL-6 and TNF-α with $IC_{50}$ values of about 8.5 and 21 nM, respectively (values reported as averages of n=15 experiments (11-6 assay) and n=4 experiments (TNF-α assay)).

Thus, Compound (I) is a potent and full transrepressor (about 90% or greater maximal inhibition) of the endogenous production of the pro-inflammatory proteins IL-6 and TNFα. In addition, Compound (I) displays only partial agonist activity (about 50% or less maximal efficacy) in inducing GR/GRE-mediated gene transcription. Thus, Compound (I) displays a differentiated profile by inducing full GR-mediated transrepression, yet only partially inducing GR/GRE-mediated transactivation. Furthermore, in assays examining the effects on functional modulation of other steroid receptors, Compound (I) displays only limited activity in activating gene expression mediated by AR, MR, and PR.

Animal Models:

1. Carrageenan-induced Paw Edema (CPE) Model

Carrageenans are a group of polysaccharides which can induce an acute inflammatory response in animals. Cardinal signs of inflammation including edema, hyperalgesia and erythema are developed in the injection site immediately following injection. The CPE model is a recognized model of inflammation and can be used to evaluate the anti-inflammatory effects of glucocorticoid receptor ligands.

To evaluate the anti-inflammatory effects of Compound (I), the compound is formulated in a vehicle comprising 0.5% carboxymethyl cellulose and 0.25% Tween 80 and administered orally via gavage to male Sprague-Dawley rats (180-200 g). For comparison, prednisolone may be administered orally in the same vehicle. Two hours later, 1% carrageenan in 50 µl of 0.9% pyrogen free saline is injected into the subplantar regions of the right hind paw. Rats are euthanized by $CO_2$ at 3 hours after the carrageenan injection. Paws are removed then weighed using a microbalance. Paws are then dissected by making several cuts on the paw surface and immediately immersing into liquid nitrogen until frozen. Frozen paws are then centrifuged to extract the exudates. Exudate levels of IL-1β, a cytokine generated during the inflammatory response is then measured by ELISA according to manufacturers instructions. Total paw protein is also measured using a protein assay kit and the absolute level of IL-1β is normalized to yield a concentration value of ng IL-1β/mg total protein.

Compound (I) inhibited carrageenan induced paw weight gain with an $ED_{50}$ of about 2.8 mg/kg. Compound (I) also reduced Paw exudate levels of IL-1β with an $ED_{50}$ of about 3.2 mg/kg. Conversely, prednisolone treatment in this model inhibited paw weight gain with an $ED_{50}$ of about 6.6 mg/kg, and reduced IL-1β levels with an $ED_{50}$ of less than about 1 mg/kg (with $ED_{50}$ values representing a mean of 5 individual determinations)

2. Serum Osteocalcin Assay

Bone loss/osteoporosis and the resulting increased risk of fracture is a common and significant adverse effect that results from glucocorticoid therapy. Glucocorticoid induced osteoporosis is believed to result, at least in part, from an inhibition of bone formation. The measurement of serum osteocalcin, a biological marker of bone synthesis, is a recognized tool for assessing the adverse effects of glucocorticoid therapy on bone.

To assess the effects of Compound (I) on bone formation, Compound (I) is formulated in a vehicle comprising 5% carboxymethyl cellulose and 0.25% Tween 80 and administered orally via gavage to sixteen week old male Swiss-Webster mice (Harlan Industries, Indianapolis) for seven days. For comparison, prednisolone is administered orally in the same vehicle. Serum is collected 24 hours after the last dose and osteocalcin levels are determined using a competitive radioimmunoassay modified to a 96 well format. Briefly, each well of a Multiscreen™ plate containing 2.5 µl mouse serum, 2.5 µl goat anti-mouse osteocalcin, 0.625 µl normal goat serum, and 119.375 µl RIA buffer (0.1225 M NaCl, 0.01 M $NaH_2PO_4$, pH 7.4, 0.025 M tetra sodium EDTA, 0.1% (w/v) BSA, and 0.1% (w/v) Tween-20) is incubated at 4° C. for 18 hours on an orbital shaker at 80 rpm. Following the addition of 0.2 µCi/ml [$^{125}$I] mouse osteocalcin in 25 µl RIA buffer to each well, the plates are incubated for 24 hours at 4° C. on an orbital shaker at 80 rpm. The complex is precipitated for 2 h at 25° C. by the addition of donkey anti-goat IgG (1:30) in 0.2 M $Na_2HPO_4$, pH 7.4, 5% (w/v) polyethylene glycol, 125 µl/well. The precipitate is collected by vacuum filtration and washed once with 100 µl/well $dH_2O$. The filters are punched and the radioactivity quantitated on a gamma counter. Radioactivity detected on the filters from test samples is inversely proportional to serum osteocalcin concentration. A standard curve of purified mouse osteocalcin is used to calculate the serum osteocalcin concentration in test samples.

Comparing daily dosages approximating the $ED_{50}$ values determined in the rat CPE model (3 mg/Kg/day for Compound (I) and 10 mg/Kg/day for prednisolone), Compound (I) induced less reduction in serum osteocalcin levels than prednisolone.

Methods for preparing Compound (I) are known in the art. For example, WO 04/052847 provides general procedures which may be employed. Furthermore, WO 05/066161 provides additional general procedures which may be employed. The following Schemes, Intermediates, and Examples further illustrate the invention and represent typical syntheses of Compound (I). The reagents and starting materials are readily available to, or may be readily synthesized by, one of ordinary skill in the art. It should be understood that the Schemes, Intermediates, and Examples are set forth by way of illustration and not limitation, and that modifications may be made by one of ordinary skill in the art. The names of the compounds of the present invention are generally obtained from ChemDraw Ultra™, version 7.0.1.

As used herein "DMSO" refers to dimethyl sulfoxide; "DIAD" refers to diisopropyl azodicarboxylate; "ADDP" refers to 1,1'-(azodicarbonyl)dipiperidine; "THF" refers to tetrahydrofuran; "DMF" refers to dimethyl formamide; "TMSCN" refers to trimethylsilyl cyanide; "TEA" or "$Et_3N$" refers to triethyl amine; "DME" refers to 1,2-dimethoxyethane; "AcOEt" refers to ethyl acetate; "pyr" refers to pyridine; "MsCl" refers to methanesulfonyl chloride "$Et_2NH$" refers to diethyl amine; "MeOH" refers to methanol; "$PhCH_3$" refers to toluene; "PhH" refers to benzene; "$PBu_3$" refers to tributylphosphine; "$PPh_3$" refers to triphenylphosphine; "dppf" refers to 1,1'-bis(diphenylphosphanyl) ferrocene, "NaO-t-Bu" refers to sodium tert-butoxide;

Scheme I

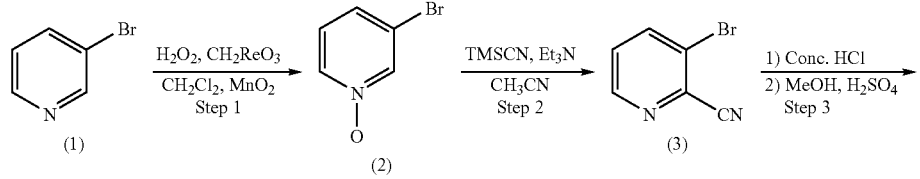

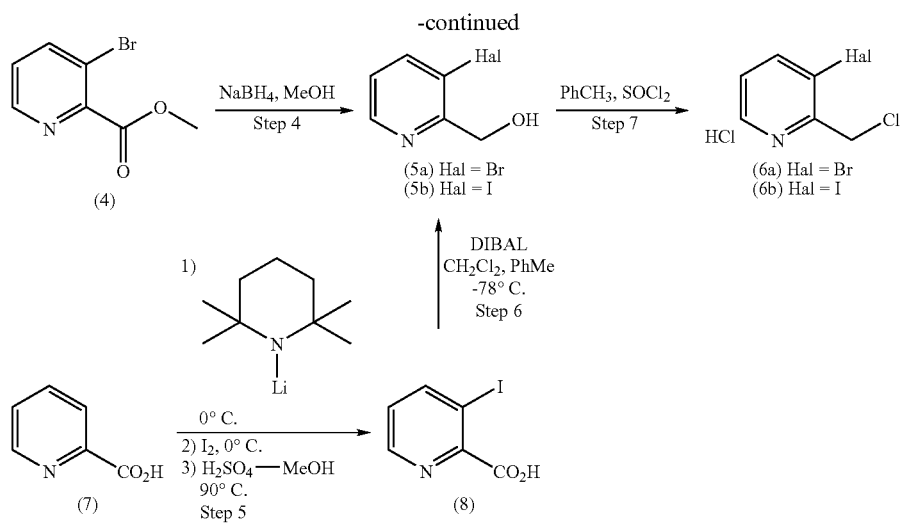

In Scheme I is described the preparation of pyridine intermediates (5) and (6). In Scheme I, Step 1, 3-bromopyridine (1) is oxidized to 3-bromo-pyridine-N-oxide (2). In Scheme I, Step 2, cyanide addition gives 3-bromo-pyridine-2-carbonitrile (3). The nitrile of formula (3) is hydrolyzed to the carboxylic acid and esterified with acid catalysis to the ester of formula (4). In Scheme I, Step 4, the ester is reduced to the pyridylmethanol of formula (5a) using sodium borohydride.

A pyridinylmethanol of formula (5b), wherein Hal=I, is accessed as shown in Scheme I, Step 5, by forming the dianion of picolinic acid (7) followed by electrophilic quenching with iodine to give 3-iodopicolinic acid (8). In Step 6, the acid of formula (8) is reduced using diisobutylaluminum hydride to provide a pyridylmethanol of formula (5b).

In Scheme I, Step 7, the alcohol of formula (5a,b) is elaborated to a pyridylmethylchloride of formula (6a,b) using thionyl chloride.

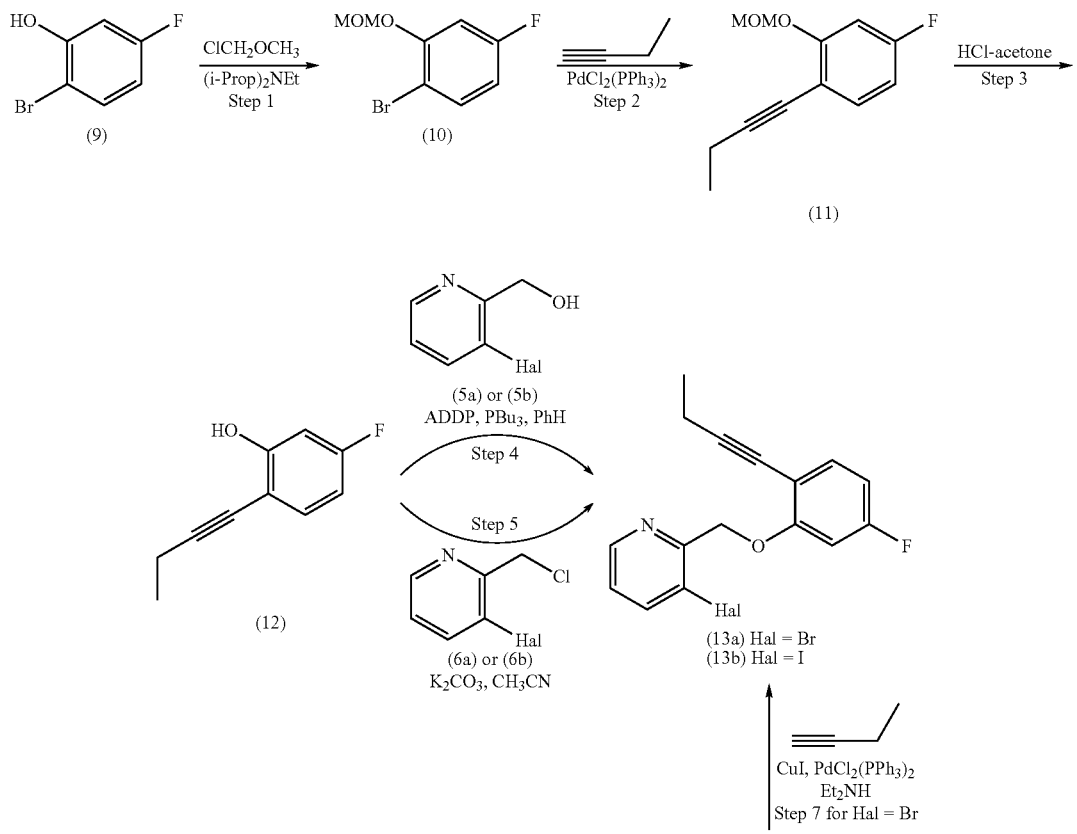

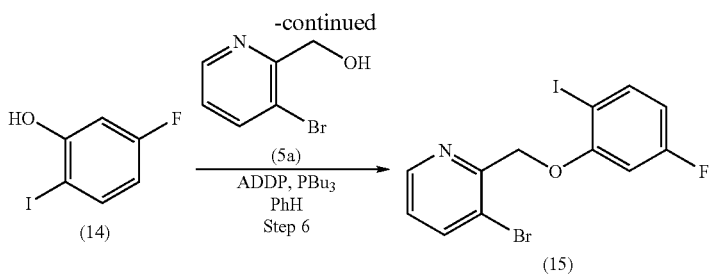

In Scheme II is described various methodologies for synthesizing key intermediate (13a,b). In Scheme II, Step 1,5-fluoro-3-bromo-phenol (9) is protected to give the methoxymethyl (MOM) ether of formula (10). In Scheme II, Step 2, a Sonagashira coupling between a protected bromophenol of formula (10), and 1-butyne provides an aryl alkyne of formula (II). The reaction can be carried out with either diethylamine or triethylamine. Aryl bromides couple at elevated temperatures (70° C.) and aryl iodides couple at room temperature. The phenol is deprotected, as shown in Scheme I, Step 3, using HCl-acetone to give the phenol of formula (12). Alternatively the phenol is protected as the THP ether and deprotected using pyridinium p-toluenesulfonate (PPTS) in methanol to give the phenol of formula (12).

In Scheme II, Step 4 a Mitsunobu reaction between a alkynyl phenol of formula (12) and a pyridinemethyl alcohol of formula (5) or (5b) gives a halopyridyl aryl alkyne of formula (13a,b). Other suitable reagents include DIAD and triphenylphosphine in THF. Alternatively, in Step 5, the halopyridyl aryl alkyne of formula (13a,b) is accessed by means of an alkylation of a phenol of formula (12) with a pyridinemethyl chloride of formula (6a) or (6b) using potassium carbonate in acetonitrile.

Another route to the bromopyridyl aryl alkyne of formula (13a) is shown in Steps 6 and 7. In Scheme II, Step 6,5-fluoro-2-iodophenol (Morice, C., et. al. *Tetrahedron Lett.* 2001, 42, 6499-6502) is coupled in a Mitsunobu reaction with the pyridylmethanol of formula (5a) to give the iodoaryl ether of formula (15). In Scheme II, Step 7, the iodoaryl ether undergoes the Sonagashira coupling with 1-butyne to give the halopyridyl aryl alkyne of formula (13a).

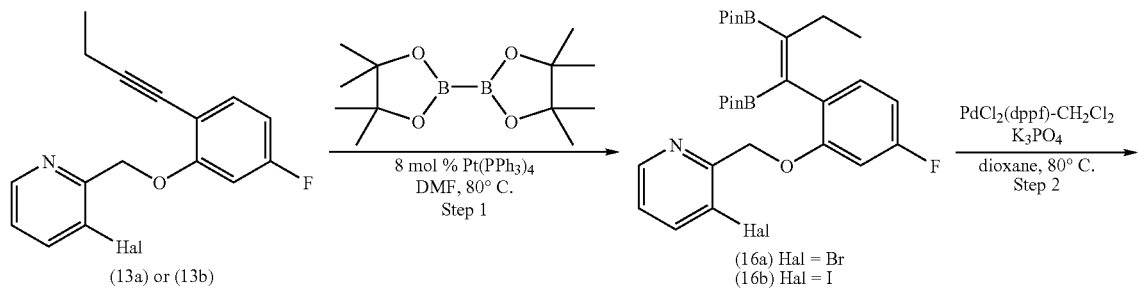

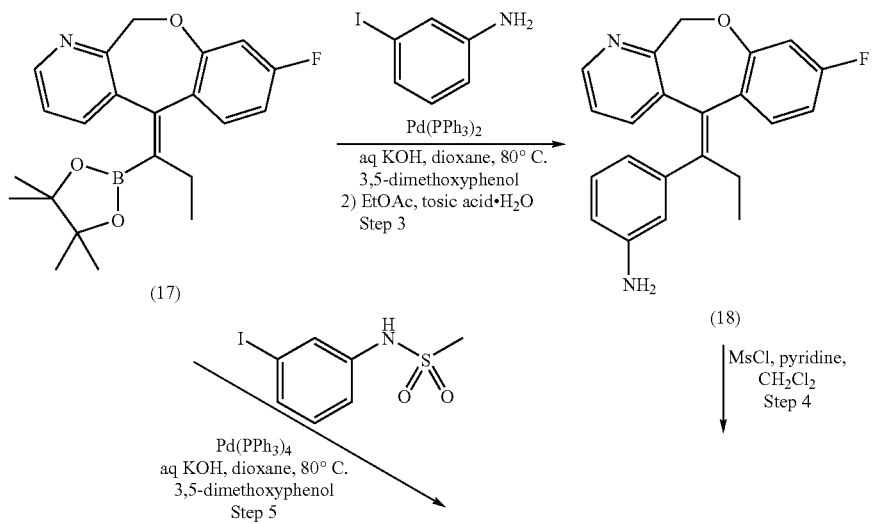

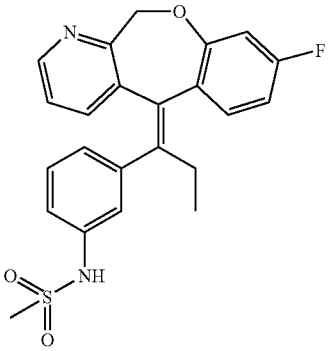

(19)

In Scheme III, Steps 1 and 2, platinum-catalyzed diboronation of a halopyridyl aryl alkyne of formula (13a,b) gives a diboronic acid of formula (16a,b) which forms a vinyl boronic acid of formula (17) upon an intramolecular Suzuki coupling under dilute conditions (ca. 0.01 M). It should be noted that the diboronation is optimal for (13a) wherein Hal=Br.

In Scheme II, Step 3, an intermolecular Suzuki coupling between vinyl boronic acid (17) and 3-iodoaniline affords the aniline benzopyridyl-10-oxepin of formula (18). In Step 4, the aniline of formula (18) is sulfonylated with methanesulfonyl chloride to give the final benzopyridyl-10-oxepin of formula (19). Alternatively, in Scheme III, Step 5 the benzopyridyl-10-oxepin of formula (19) is accessed directly by doing the Suzuki coupling with N-(3-iodo-phenyl)-methanesulfonamide.

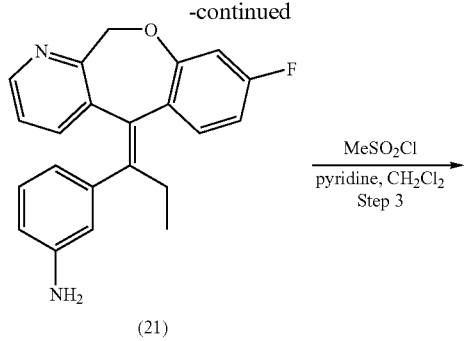

(21)

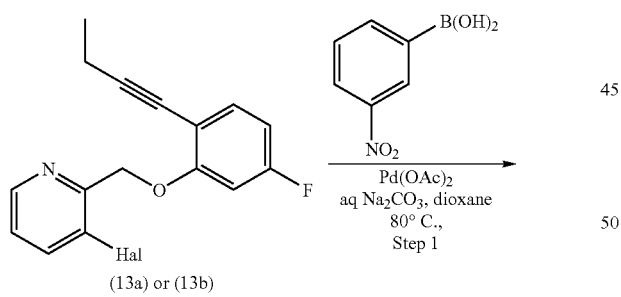

(13a) or (13b)

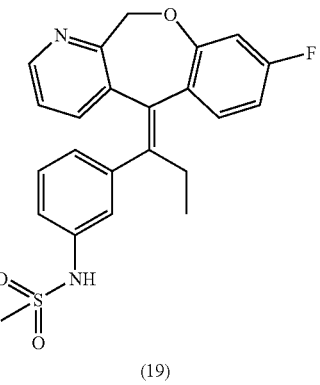

(19)

In Scheme IV is yet another method for obtaining the benzopyridyl-10-oxepin of formula (19). In Scheme IV, Step 1, sequential intramolecular Heck and Suzuki reactions of a halopyridyl aryl alkyne of formula (13a,b) with 3-nitrobenzeneboronic acid is carried out to give a nitrophenyl benzopyridyloxepin of formula (20). Yields are improved when conducting a slow addition of boronic acid to the aryl alkyne when Hal=I It will be recognized by those skilled in the art that in Steps 2-3 (19) is derived by reduction of a nitro analogue of formula (20) to give the aniline of formula (21) followed by sulfonylation.

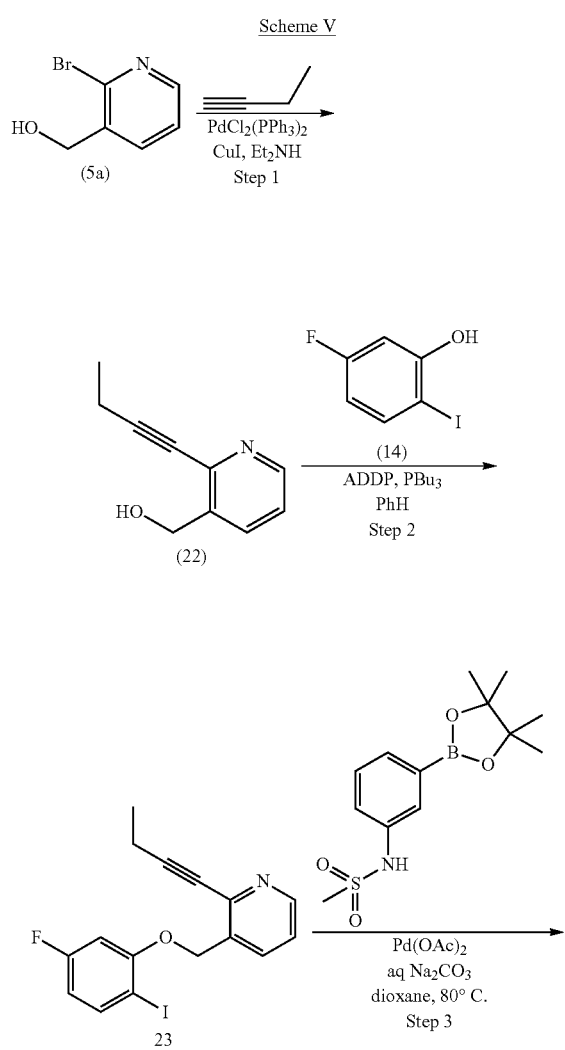
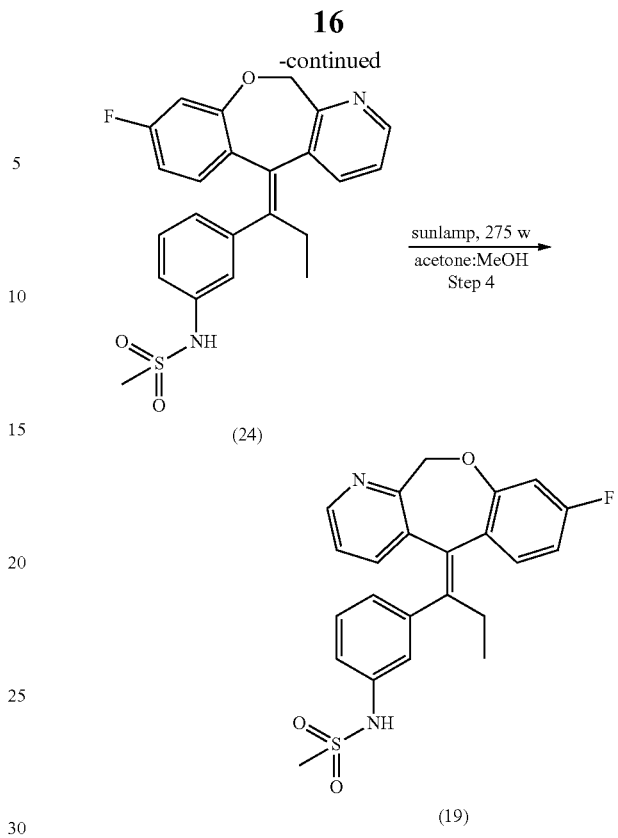

In Scheme V, Step 1, a Sonagashira coupling occurs between a 2-bromopyridine of formula (5a) and 1-butyne in similar fashion as in Scheme 2, Step 2 to give an alkynyl pyridylmethyl alcohol of formula (22). In Scheme V, Step 2 a Mitsunobu reaction between a pyridylmethyl alcohol of formula (22), and 5-fluoro-2-iodophenol of formula (14) gives a pyridine of formula (23). In Step 3, an intramolecular Heck reaction followed by Suzuki cross coupling with N-[3-(4,4,5,5-tetramethyl-[1,3,2]dioxaborolan-2-yl)-phenyl]-methanesulfonamide affords a benzopyridyl-11-oxepin of formula (24), which is photoisomerized to the benzopyridyl-10-oxepin of formula (19).

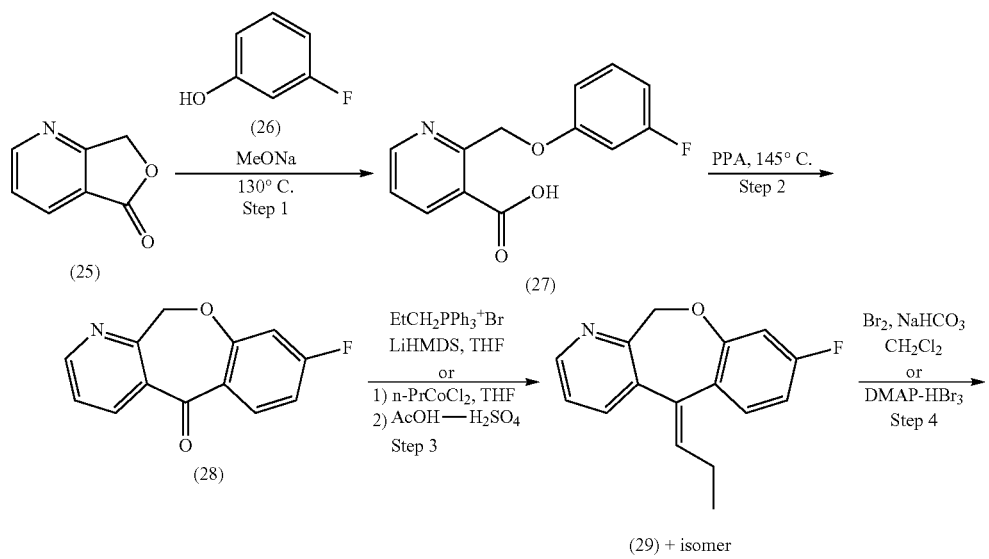

-continued

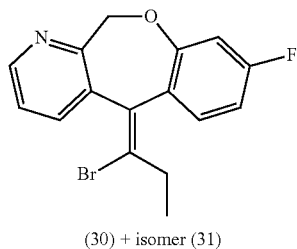

(30) + isomer (31)

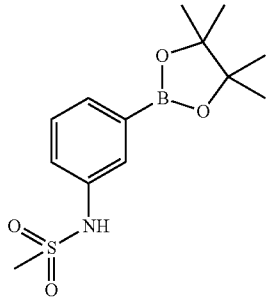

Pd(PPh₃)₄
aq Na₂CO₃
dioxane, 90° C.

Step 5

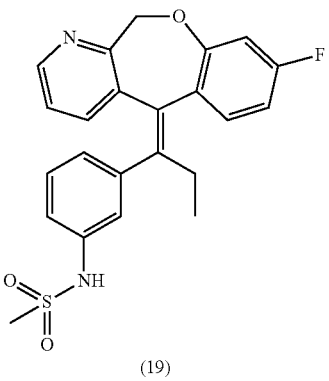

(19)

275 w sunlamp
Step 7

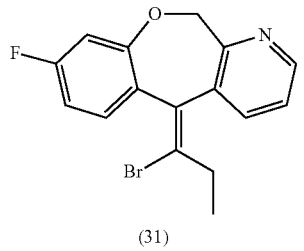

(31)

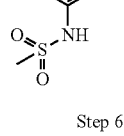

Pd(PPh₃)₄
aq Na₂CO₃
dioxane, 90° C.

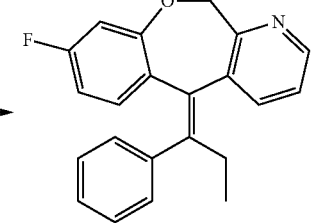

(24)

Step 6

In Scheme VI, Step 1, a lactone of formula (25) is reacted with the sodium salt of a halophenol of formula (26) to afford the acid of formula (27). In Scheme VI, Step 2, a Friedel-Crafts reaction is carried out with the benzoic acid of formula (27) to give a benzopyridyloxepinone of formula (28). In Scheme IV, Step 3, the ketone of formula (28) is converted to an alkenylbenzopyridyloxepin of formula (29) as a mixture of geometric isomers via either a Wittig olefination or an alkylcerium addition/dehydration sequence. In Step 4, alkenylbenzopyridyloxepin of formula (29) and its isomer are reacted with either bromine or 4-(dimethylamino)pyridinium tribromide to give geometric vinyl bromides of formulae (30) and (31). The vinyl bromides are separated and converted to their respective sulfonamides (19) or (24), as shown in Steps 5 and 6, via Suzuki cross coupling with N-[3-(4,4,5,5-tetramethyl-[1,3,2]dioxaborolan-2-yl)-phenyl]-methanesulfonamide under typical conditions. The sulfonamide of formula (24) is photo-isomerized to the benzopyridyl-10-oxepin of formula (19) in Scheme VI, Step 7.

Intermediate 1

1-Bromo-4-fluoro-2-methoxymethoxy-benzene

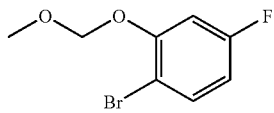

2-Bromo-5-fluorophenol (30 g, 0.16 mol) is dissolved in dichloromethane (170 mL) and cooled to 0° C. To this solution is added diisopropylethylamine (36 mL, 0.20 mol) via syringe followed by chloromethyl methyl ether (16 mL, 0.20 mol) via an addition funnel. The solution is stirred and warmed to room temperature. After 2 h, the mixture is washed with saturated aqueous NH₄Cl, water, and brine. The organic portion is dried over MgSO₄, filtered, and concentrated under reduced pressure. The resulting residue is purified by flash chromatography (Biotage® Si65M, 20% AcOEt/hexane) to yield 26.1 g (71%) of the title compound as a clear colorless oil. ¹H NMR 400 MHz (CDCl₃) δ 7.46-7.53 (m, 1H), 6.92-6.99 (m, 1H), 6.63-6.70 (m, 1H), 5.26 (s, 2H), 3.55 (s, 3H).

Intermediate 2

1-But-1-ynyl-4-fluoro-2-methoxymethoxy-benzene

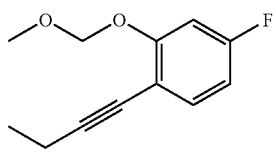

1-Bromo-4-fluoro-2-methoxymethoxy-benzene (7.6 g, 32 mmol) is placed in a pressure flask, dissolved in diethylamine (65 mL) and degassed with nitrogen for 15 min. An excess of butyne is bubbled through the solution, CuI (1.9 g, 10 mmol) and PdCl₂(PPh₃)₂ (2.3 g, 3.3 mmol) are added, and the flask is heated to 70° C. for 44 h. The mixture is diluted with ether, then washed with saturated aqueous NH₄Cl and brine. The organic portion is dried over MgSO₄, filtered, and concentrated under reduced pressure. The resulting residue is purified by flash chromatography (Biotage® Si65M, 3% THF/hexane) to provide 6.12 g (91%) of the title compound as an orange solid. GCMS m/e 208 [M]⁺.

Intermediate 3

2-But-1-ynyl-5-fluoro-phenol

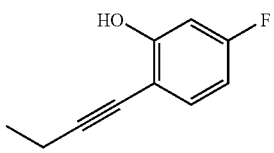

1-But-1-ynyl-4-fluoro-2-methoxymethoxy-benzene (6.1 g, 29 mmol) is dissolved in 250 mL of a 10% solution of concentrated HCl in acetone. The solution is stirred at room temperature for 5 h. The reaction is diluted with ether and washed with saturated aqueous NaHCO₃ and brine. The organic portion is dried over MgSO₄, filtered, and concentrated under reduced pressure. The resulting residue is purified by flash chromatography (Biotage® Si65M, 5% AcOEt/hexane) to yield 3.52 g (73%) of the title compound as an orange oil. GCMS m/e 164[M]⁺.

Intermediate 4

3-Bromo-pyridine 1-oxide

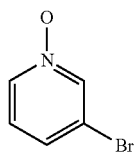

Methyltrioxorhenium (100 mg, 0.401 mmol) is dissolved in dichloromethane (40 mL) and 3-bromopyridine (15.8 g, 100 mmol) is added followed by 30% aqueous H₂O₂ (22.7 mL). The biphasic mixture is stirred at room temperature. After 18 h MnO₂ (25 mg, 0.29 mmol) is added and the mixture is stirred at room temperature for 2 h. The mixture is extracted with dichloromethane and the combined extracts are washed with brine, dried over MgSO₄, filtered, and concentrated under reduced pressure to yield 9.52 g (55%) of the title compound as an orange oil. GCMS m/e 174 [M−H]⁻.

Intermediate 5

3-Bromo-pyridine-2-carbonitrile

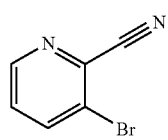

3-Bromo-pyridine 1-oxide (9.4 g, 54 mmol) is dissolved in acetonitrile (60 mL) and triethylamine (15 mL) is added followed by trimethylsilyl cyanide (21.7 mL, 163 mmol). The mixture is heated to 100° C. and stirred for 16 h. The mixture is cooled to 0° C., poured into 250 mL of 5 M aqueous NaOH, and extracted with dichloromethane. The combined extracts are washed with brine, dried over MgSO₄, filtered, and concentrated under reduced pressure. The resulting material is purified using flash chromatography (Biotage® Si65M, 20% AcOEt/hexane) yields 7.8 g (79%) of the title compound as a yellow solid. GCMS m/e 182 [M−H]⁻.

Intermediate 6

3-Bromo-pyridine-2-carboxylic acid methyl ester

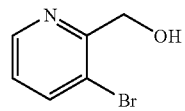

3-Bromo-pyridine-2-carbonitrile (14.7 g, 80.3 mmol) is dissolved in concentrated HCl (50 mL) and heated to 110° C. for 18 h. The mixture is cooled to 0° C., filtered, rinsed with a small amount of ether, and dried in an oven under reduced pressure. The resulting brown solid is dissolved in methanol (80 mL), concentrated H₂SO₄ (6.6 mL) is added dropwise, and the solution is heated to 90° C. for 16 h. The methanol is removed under reduced pressure, saturated aqueous sodium bicarbonate is added to obtain a basic pH, and the mixture is extracted with AcOEt. The combined extracts are washed with brine, dried over MgSO₄, filtered, and concentrated under reduced pressure to yield 12.8 g (74%) of the title compound as a white solid. GCMS m/e 215 [M−H]⁻.

Intermediate 7

(3-Bromo-pyridin-2-yl)-methanol

3-Bromo-pyridine-2-carboxylic acid methyl ester (12.8 g, 59.2 mmol) is dissolved in methanol (150 mL) and cooled to 0° C. To the mixture is added NaBH₄ (11.2 g, 296 mmol) in 1.0 g portions. The mixture is warmed to room temperature and stirred for 3 h. The methanol is removed under reduced pressure, AcOEt is added and the solution is washed with saturated, aqueous ammonium chloride and brine. The organic portion is dried over MgSO₄, filtered, and concentrated under reduced pressure to yield 6.8 g (62%) of the title compound as a white solid. GCMS m/e 187 [M−H]⁻.

Intermediate 8

3-Bromo-2-(2-but-1-ynyl-5-fluoro-phenoxymethyl)-pyridine

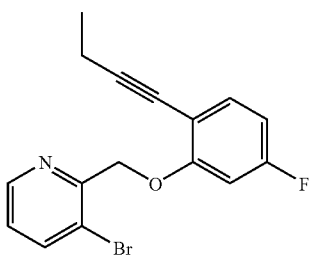

A solution of (3-bromo-pyridin-2-yl)-methanol (3.09 g, 16.43 mmol), 2-but-1-ynyl-5-fluoro-phenol (2.70 g, 16.43 mmol), and triphenylphosphine (6.46 g, 24.64 mmol) in dichloromethane (162 mL) is cooled to −5 to 0° C. Diisopropyl azodicarboxylate (DIAD) is added (4.85 mL, 24.64 mmol) dropwise over a 15 min period. After 1 h the solvent is evaporated and the crude material directly purified by flash chromatography (SiO$_2$; 4% hexane: AcOEt) to give 3.5 g (64%) of the title compound. LCMS m/e 334 [M+H]$^+$.

Intermediate 9

8-Fluoro-5-[1-(3-nitro-phenyl)-propylidene]-5,1'-dihydro-10-oxa-1-aza-dibenzo[a,d]cycloheptene

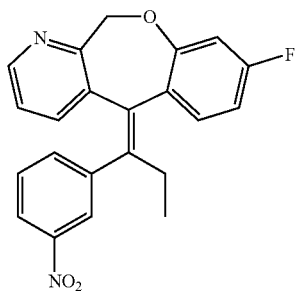

Pd(OAc)$_2$ (0.18 g, 5%) and o-tolyl phosphine (0.32 g, 1.05 mmol) are added to a solution of 3-bromo-2-(2-but-1-ynyl-5-fluoro-phenoxymethyl)-pyridine (3.50 g, 10.5 mmol), sodium carbonate (3.39 g, 31.5 mmol) and 3-nitrobenzeneboronic acid (2.27 g, 13.6 mmol) in 4:1 dioxane:water (101 mL). Nitrogen is bubbled through the mixture for 15 min and then the reaction is stirred at 75° C. overnight. The mixture is cooled to room temperature and solids are filtered though Celite®. Water and AcOEt are added and the phases are decanted. The aqueous layer is extracted with AcOEt and the combined organic layers are dried over magnesium sulfate, filtered and concentrated under reduced pressure. The resulting residue is purified by flash chromatography (SiO$_2$, 20% AcOEt:hexanes) to afford 1.49 g (38%) of the title compound. LCMS m/e 377 [M+H]$^+$.

Intermediate 10

3-[1-(8-Fluoro-1H-10 oxa-1-aza-dibenzo[a,d]cyclohepten-5-ylidene)-propyl]-phenylamine

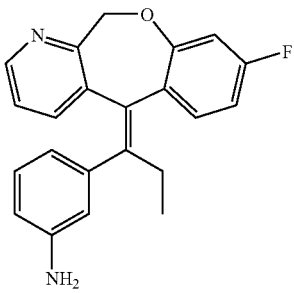

8-Fluoro-5-[1-(3-nitro-phenyl)-propylidene]-5,11-dihydro-10-oxa-1-aza-dibenzo[a,d]cycloheptene (1.49 g, 3.96 mmol) is dissolved in ethanol (20 mL) and purged with nitrogen. Pd/C (0.15 g, 10%) is added and the mixture hydrogenated under 1 atm of hydrogen for 2 h. The mixture is purged with nitrogen, filtered though Celite®, and the solids are washed with ethanol. The filtrate is concentrated under reduced pressure to obtain 1.37 g (99%) of the title compound. LCMS m/e 347 [M+H]$^+$.

EXAMPLE 1

N-{3-[1-(8-Fluoro-11H-10-oxa-1-aza-dibenzo[a,d]cyclohepten-5-ylidene)-propyl]-phenyl}-methanesulfonamide

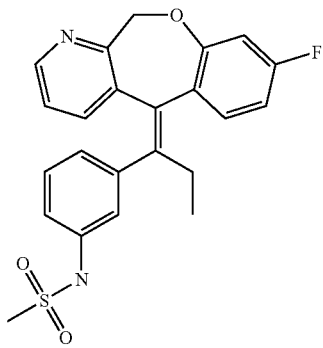

Methanesulfonyl chloride (0.34 mL, 4.36 mmol) is added dropwise to a solution of 3-[1-(8-fluoro-11H-10-oxa-1-aza-dibenzo[a,d]cyclohepten-5-ylidene)-propyl]-phenylamine (1.37 g, 3.96 mmol) and pyridine (0.35 mL, 4.36 mmol) in dichloromethane (10 mL) at 0° C. After 2 h, 7% aqueous sodium bicarbonate (20 mL) is added and the mixture stirred for 30 min, decanted, and the layers separated. The aqueous phase is washed with dichloromethane (2×20 mL). The organic phases are collected and washed with brine, dried over sodium sulfate, filtered and concentrated under reduced pressure to obtain 1.98 g of crude product. The material is purified by flash chromatography, using Biotage® and eluting with hexane:ethanol (9:1) to afford 1.35 g (80%) of the title compound. LCMS m/e 425 [M−H]$^+$.

What is claimed is:

1. A compound which is (E)-N-{3-[1-(8-Fluoro-11H-10-oxa-1-aza-dibenzo[a,d]cyclohepten-5-ylidene)-propyl]-phenyl}-methanesulfonamide, or a pharmaceutically acceptable salt thereof.

2. The compound according to claim 1 which is (E)-N-{3-[1-(8-Fluoro-11H-10-oxa-1-aza-dibenzo[a,d]cyclohepten-5-ylidene)-propyl]-phenyl}-methanesulfonamide.

3. A method of treating rheumatoid arthritis, comprising administering to a patient in need thereof an effective amount of a compound which is (E)-N-{3-[1-(8-Fluoro-11H-10-oxa-1-aza-dibenzo[a,d]cyclohepten-5-ylidene)-propyl]phenyl}-methanesulfonamide, or a pharmaceutically acceptable salt thereof.

4. The method according to claim 3 comprising administering to a patient in need thereof an effective amount of a compound which is (E)-N-{3-[1-(8-Fluoro-11H-10-oxa-1-aza-dibenzo[a,d]cyclohepten-5-ylidene)-propyl]-phenyl}-methanesulfonamide.

5. A pharmaceutical composition comprising a compound which is (E)-N-{3-[1-(8-Fluoro-11H-10-oxa-1-aza-dibenzo[a,d]cyclohepten-5-ylidene)-propyl]-phenyl}-methanesulfonamide, or a pharmaceutically acceptable salt thereof, in combination with one or more pharmaceutically acceptable carriers, excipients, or diluents.

6. The pharmaceutical composition of claim 5 comprising a compound which is (E)-N-{3-[1-(8-Fluoro-11H-10-oxa-1-aza-dibenzo[a,d]cyclohepten-5-ylidene)-propyl]-phenyl}-methanesulfonamide, in combination with one or more pharmaceutically acceptable carriers, excipients, or diluents.

* * * * *

UNITED STATES PATENT AND TRADEMARK OFFICE
CERTIFICATE OF CORRECTION

| | | |
|---|---|---|
| PATENT NO. | : 8,101,761 B2 | |
| APPLICATION NO. | : 12/810886 | |
| DATED | : January 24, 2012 | |
| INVENTOR(S) | : Matthew William Carson et al. | |

It is certified that error appears in the above-identified patent and that said Letters Patent is hereby corrected as shown below:

On the Title page, Col. 1, Item [54] (title), Line 2, please delete "DIBENZO [A,D]" and insert --DIBENZO[A,D]--, therefor.

On the Title page, Item [56] Col. 2, (Other Publications), line 14, please delete "Cyclocarbopalldation" and insert --Cyclocarbopalladation--, therefor.

In Column 1, line 2, please delete "DIBENZO [A,D]" and insert --DIBENZO[A,D]--, therefor.

In Column 23, line 12, in Claim 3, please delete "propyl]phenyl}" and insert --propyl]-phenyl)--, therefor.

Signed and Sealed this
Twentieth Day of March, 2012

David J. Kappos
*Director of the United States Patent and Trademark Office*